United States Patent
Gotoh et al.

(10) Patent No.: US 9,304,108 B2
(45) Date of Patent: Apr. 5, 2016

(54) QUENCHING DEPTH MEASUREMENT METHOD AND QUENCHING DEPTH MEASUREMENT APPARATUS

(75) Inventors: Yuji Gotoh, Oita (JP); Noriyoshi Takaoka, Kanagawa-ken (JP); Kazuhiro Kawasaki, Kanagawa-ken (JP); Yoshitaka Misaka, Kanagawa-ken (JP)

(73) Assignees: NETUREN CO., LTD., Tokyo (JP); NATIONAL UNIVERSITY CORPORATION OITA UNIVERSITY, Oita (JP)

(*) Notice: Subject to any disclaimer, the term of this patent is extended or adjusted under 35 U.S.C. 154(b) by 383 days.

(21) Appl. No.: 13/881,444

(22) PCT Filed: Oct. 26, 2011

(86) PCT No.: PCT/JP2011/074709
§ 371 (c)(1),
(2), (4) Date: Jul. 9, 2013

(87) PCT Pub. No.: WO2012/057224
PCT Pub. Date: May 3, 2012

(65) Prior Publication Data
US 2013/0300405 A1    Nov. 14, 2013

(30) Foreign Application Priority Data
Oct. 26, 2010   (JP) .................................. 2010-239894

(51) Int. Cl.
G01N 27/80    (2006.01)
G01N 27/72    (2006.01)

(52) U.S. Cl.
CPC ................ *G01N 27/80* (2013.01); *G01N 27/72* (2013.01)

(58) Field of Classification Search
CPC ....................................................... G01N 27/80
USPC ......................................... 324/239, 232, 240
See application file for complete search history.

(56) References Cited

U.S. PATENT DOCUMENTS

2010/0163138 A1*  7/2010  Beppu et al. .................. 148/537

FOREIGN PATENT DOCUMENTS

| JP | 2002-014081 | 1/2002 | |
| JP | 2009-109358 | 5/2009 | |
| JP | 2010-164306 | 7/2010 | |
| JP | 2010164306 A * | 7/2010 | ............. G01N 27/80 |

OTHER PUBLICATIONS

Yuji Goto et al., "Examination of measuring method of surface hardness of hardened steel using 3DFEM considering non-uniform initial relative permeability and conductivity", The Papers of Joint Technical Meeting on Static Apparatus and Rotating Machinery, IEE Japan, Sep. 6, 2003, pp. 83-88.
Yuji Goto et al., "Numerical Analysis for Evaluating Surface Hardened Depth Magnetic Testing Considering the Heterogeneity of Permeability", Journal of JSNDI, 2001, vol. 50, Apr. 1, 2001, pp. 241-248.
Akihisa Kameari, "Calculation of Transient 3D Eddy Current Using Edge-Elements", IEEE Transactions on Magnetics, vol. 26, No. 2, Mar. 1990, pp. 466-469.

* cited by examiner

*Primary Examiner* — Arleen M Vazquez
*Assistant Examiner* — Brent J Andrews
(74) *Attorney, Agent, or Firm* — Greenblum & Bernstein, P.L.C.

(57) ABSTRACT

A quenching depth measuring method is used for measuring the quenching depth in a workpiece and includes the steps of: magnetizing the workpiece by disposing, in the vicinity of the workpiece, a magnetizer equipped with an exciting coil; detecting, through a detection coil, an induced magnetic field generated by the magnetization; measuring the induced magnetic field as the output voltage of the detection coil; and specifying the thickness of the quenched hardened layer of the workpiece on the basis of known electromagnetic characteristic information of an unquenched material and a fully-quenched material and an output voltage value measured by the detection coil, the unquenched material being made of the same material as the constituent material of the workpiece and being a material on which a quenching process is not performed, the fully-quenched material being a material on which the quenching process is performed.

2 Claims, 4 Drawing Sheets

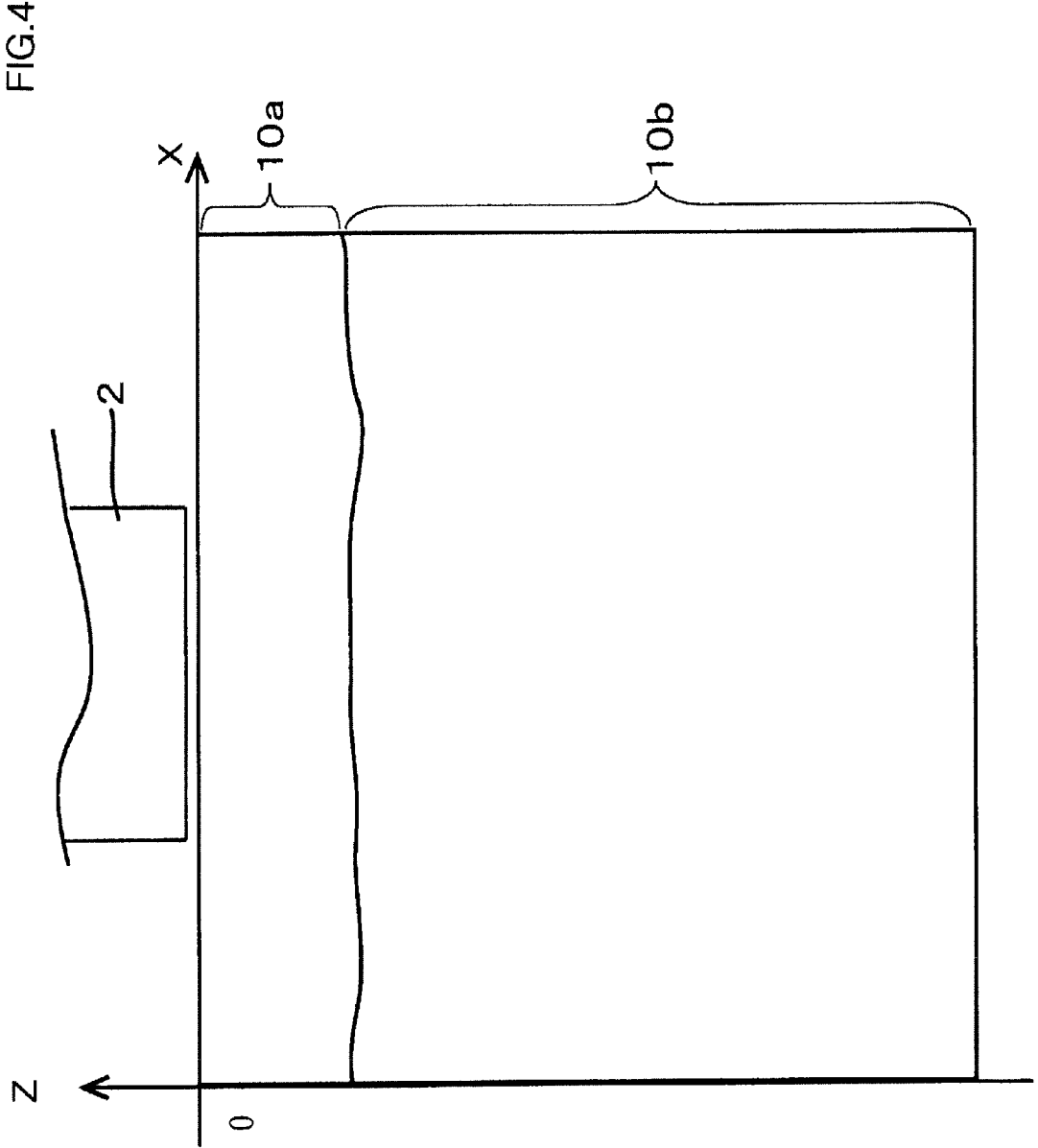

QUENCHING DEPTH MEASUREMENT METHOD AND QUENCHING DEPTH MEASUREMENT APPARATUS

TECHNICAL FIELD

The present invention relates to a nondestructive inspection method of quenching depth in a quenched workpiece and to a quenching depth measurement apparatus.

BACKGROUND ART

High frequency quenching may be applied to harden a workpiece, such as a steel material, to increase the strength of the metal. As mechanical characteristics vary corresponding to the depth of a quench hardened layer, quenching is carried out under preset process conditions, and quality inspection is further carried out after the manufacturing. Conventionally, an example of a method of inspecting whether appropriate quenching is applied to the workpiece or not includes a method of cutting and inspecting an arbitrarily extracted workpiece. In the method, much time is required for the inspection, and the workpiece to be inspected cannot be used as a product. Further, a problem that inspection on all of the workpieces cannot be performed exists. Therefore, a method of nondestructive inspection of a quenching state of a workpiece has been investigated.

Document Cited 1 adopts a method in which permeability is measured on a workpiece made of carbon steel in an axis-symmetrical shape by passing through an induction coil, quenching depth in each cross section of the workpiece is estimated, a surface hardness tester is used to measure surface hardness, and a position with a significant increase in the surface hardness is detected to specify an end point of a quenching range to thereby inspect a quenching pattern of the workpiece.

Document Cited 2 relates to a nondestructive measurement method of depth of a quench hardened layer of a steel material, wherein a low frequency AC magnetic field generated by an excitation coil magnetizes the steel material in a direction along the surface to generate eddy current, a detection coil detects an induction magnetic field induced by the eddy current, and an output voltage of the detection coil is compared with known data to estimate the depth of the quench hardened layer of a symmetrical steel material.

DOCUMENTS CITED

Patent Documents

[Document Cited 1] Japanese Patent Laid-Open No. 2009-109358
[Document Cited 2] Japanese Patent Laid-Open No. 2002-14081

SUMMARY OF INVENTION

Problem To Be Solved

In the measurement method of the quenching pattern disclosed in Document Cited 1, the workpieces to be measured are limited to an axis-symmetrical workpiece. Next, as the workpiece is passed inside of the induction coil, the size of the workpiece that can be measured is limited. Or the size of the induction coil and the size of the workpiece should be adjusted, efficiency may be poor. Furthermore, as the method requires a calibration curve obtained in advance by experiment or the like for each of a plurality of measurement positions, and the surface hardness tester is used to specify the quenching range supported by the eddy current measurement to measure the whole image of the practical quenching pattern, a large number of man-hours are required for the nondestructive inspection.

In the measurement method disclosed in Document Cited 2, an equivalent sine wave alternating current nonlinear analysis method is employed to evaluate the output voltage obtained by the detection coil when the cylindrical high frequency quenching material is inserted to the probe. Therefore, as the quenching depth obtained by the analysis is an axis-symmetrical value, the technology can be applied to measuring objects having axis-symmetrical shapes only, and the measurement accuracy is poor. In the analysis method disclosed in Document Cited 2, as the correlation between the permeability and the applied magnetic flux density cannot be appropriately acquired, the method is not suitable for nondestructive inspection because of a deviation from the actual measurement value. Next, as the measurement method disclosed in Document Cited 2 assumes that there are four levels of hardness depending on depth from the surface of the steel material and the initial magnetization curve and the electric conductivity of each level of hardness are used as known data to simplify the technology, the technology is not suitable for highly accurate measurement.

An object of the present invention is to provide a nondestructive inspection method that can quickly and accurately measure quenching depth of a quenched material.

Means To Solve the Problem

As a result of intensive studies, the present inventors have achieved the object by adopting the following quenching depth measurement method and quenching depth measurement apparatus.

A quenching depth measurement method according to the present invention is the method of measuring quenching depth in a workpiece, the method is characterized in including: magnetize the workpiece by arranging a magnetizer including an excitation coil near the workpiece; detecting an induction magnetic field generated by the magnetization by a detection coil to measure an output voltage of the detection coil; and specifying thickness of a quench hardened layer of the workpiece based on known electromagnetic characteristic information on both an unquenched material not subjected to quenching and a completely quenched material subjected to quenching both are made of a workpiece equivalent material and an output voltage value measured by the detection coil.

The quenching depth measurement method according to the present invention is more preferable that the electromagnetic characteristic information includes an estimated output voltage value of the detection coil obtained by analysis based on a finite element method using initial magnetization curves and electric conductivities of both the unquenched material and the completely quenched material of a workpiece equivalent material.

The quenching depth measurement apparatus according to the present invention is characterized in including: a magnetizer that magnetizes a workpiece;
means for detecting an induction magnetic field generated by the magnetization by a detection coil to measure an output voltage of the detection coil; and quenching depth specifying mean for calculating quenching depth of the workpiece from a measured output voltage value of the detection coil and known magnetic characteristic information relating to a workpiece equivalent material, wherein the quenching depth specifying mean specifies the quenching depth of the workpiece from the known electromagnetic characteristic information including an estimated output voltage value of the detection coil obtained by analysis based on a finite element method using initial magnetization curves and electric conductivities on both an unquenched material not subjected to quenching and a completely quenched material subjected to quenching and the output voltage value of the detection coil.

Advantage of the Invention

In the quenching depth measurement method and the quenching depth measurement apparatus according to the present invention, as the thickness of the quench hardened layer can be specified based on the known electromagnetic characteristic information and the output voltage value of the detection coil, workpiece for preparation of calibration curve that is necessary in the conventional nondestructive inspection is dispensable, the quenching thickness of the workpiece can be inspected by nondestructive inspection simple and highly accurate.

Further, quenching depth data obtained by using the quenching depth measurement method and the quenching depth measurement apparatus according to the present invention can create a calibration curve (hereinafter, "FEM calibration curve"). The FEM calibration curve can be used as a calibration curve of another quenching depth measurement method using a self induction method and a relative measurement method, and preparation of calibration curve required in other measurement methods can be omitted.

BRIEF DESCRIPTION OF DRAWINGS

FIG. 4 is a schematic diagram demonstrating the quenching depth measurement method according to the present invention.

DETAILED DESCRIPTION OF EMBODIMENTS

A preferred embodiment of a quenching depth measurement method according to the present invention will be described. The quenching depth measurement method according to the present invention is a nondestructive measurement method of quenching depth in a workpiece made of a magnetic material, wherein the workpiece is magnetized to generate eddy current, a detection coil measures a magnetic field of the workpiece, and the quenching depth of the workpiece is estimated based on a measurement result. In the quenching depth measurement method according to the present invention, a magnetizer including an excitation coil is arranged near the workpiece to magnetize the workpiece, then the detection coil measures an output voltage of the magnetized workpiece, and thickness of a quench hardened layer of the workpiece is specified based on known electromagnetic characteristic information on both an unquenched material not subjected to quenching and a completely quenched material subjected to quenching both are made of a workpiece equivalent material and based on an output voltage value measured by the detection coil.

Figure 1:
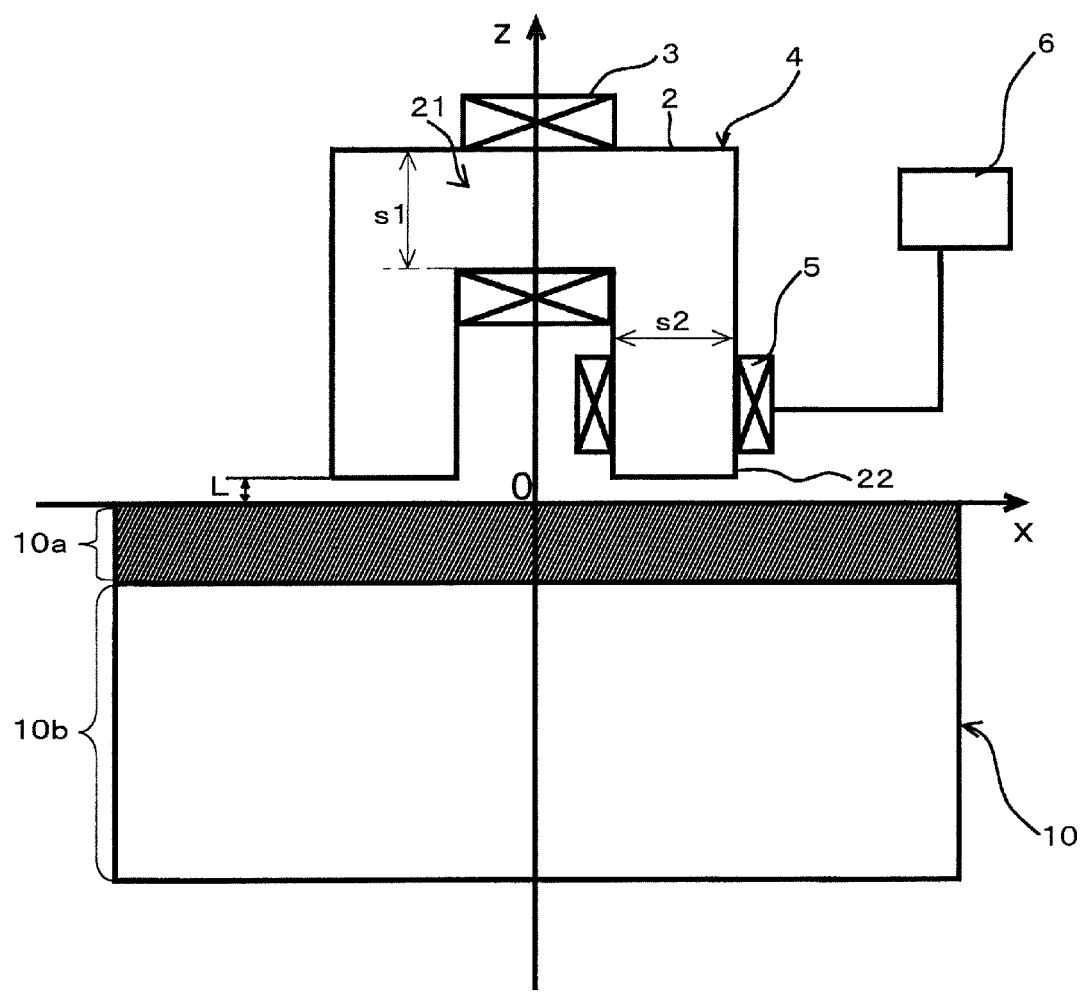
FIG. 1 is a schematic diagram demonstrating a quenching depth measurement method according to the present invention.

FIG. 1 is a schematic diagram demonstrating one example of a quenching depth measurement method according to the present invention. A workpiece 10 is a quenched steel material. A magnetizer 4 includes an excitation coil 3 that magnetizes the workpiece 10; and current supply to the excitation coil 3 magnetizes the workpiece 10. In the example shown in FIG. 1, current supply to the excitation coil 3 wound around a yoke 2 magnetizes the workpiece 10. Next, the yoke 2 made of a ferrite material includes an excitation coil winding unit 21 substantially parallel to the surface of the workpiece 10; and an opening section 22 bent at a right angle relative to the excitation coil winding unit 21. In the example shown in FIG. 1, the yoke 2 is substantially U-shaped as viewed from the side, with both sides of the excitation coil winding unit 21 bent at a right angle. Thickness a1 of the excitation coil winding unit 21 and thickness a2 of the opening section 22 are equal, and cross-sectional areas are also equal. The excitation coil 3 is wound around the excitation coil winding unit 21 of the yoke 2, with the winding direction perpendicular to the surface of the workpiece 10.

The yoke 2 is arranged near the surface of the workpiece 10 with a specific gap L. When a certain amount of current is supplied to the excitation coil 3 in this state, the workpiece 10 is magnetized, and eddy current generates on the surface of the workpiece 10. A detection coil 5 is used for detecting an induction magnetic field generated by the magnetization of the workpiece 10 by the magnetizer 4. In the example shown in FIG. 1, the detection coil 5 is wound around the opening section 22 of the yoke 2. The detection coil 5 detects the induction magnetic field induced by the eddy current generated by the magnetization of the workpiece 10 by the magnetizer 4, and a voltmeter 6 measures an output voltage of the detection coil 4.

The electromagnetic characteristic information will be described. In the quenching depth measurement method according to the present invention, a correlation between quenching depth and electromagnetic characteristics of a workpiece equivalent material are analyzed from known electromagnetic characteristics of both an unquenched workpiece equivalent material not subjected to quenching and a completely quenched workpiece equivalent material subjected to quenching and is used as electromagnetic characteristic information. As the "known electromagnetic characteristics", values disclosed in a document, such as "Metals Handbook" by The Japan Institute of Metals and Materials can be used as unique physical properties of the workpiece equivalent material. More specifically, an estimated value of the output voltage predicted to be detected by the detection coil is obtained corresponding to the quenching depth using an analysis method described later based on standard physical properties (such as electric conductivity $\sigma$, permeability $\mu$, and initial magnetization curves) of the unquenched material (raw material) and the completely quenched material in the workpiece equivalent material as the object to be measured. The electromagnetic characteristic information can also be used for another workpiece in a different shape if the material is the same as the workpiece to be measured.

In the conventional nondestructive inspection, the destructive investigation to the object to be measured should be applied in advance to obtain the calibration curve as a basis of the measurement. On the contrary, in the quenching depth measurement method according to the present invention, the electromagnetic characteristic information obtained from the physical properties of an existing standard product can be used to specify the quenching depth by nondestructive inspection, and the man-hours of the nondestructive inspection can be reduced.

The following Expressions (1) to (3) are used to estimate the quenching depth. Magnetic flux density B(T) can be expressed by the following Expression 1. The values of the permeability μ and the electric conductivity σ are different between the quenched material and the unquenched material (raw material). Therefore, when a same magnetic field H is applied to the workpiece, the size of the magnetic flux density B shown in Expression (1) varies due to the difference between the completely quenched material and the unquenched material (raw material).

$$B = \mu H \quad (1)$$

In Expression (1), μ denotes permeability, and H denotes applied magnetic field (A/m).

Eddy current Je (A/m$^2$) can be expressed by the following Expression (2). Although eddy current is generated in an AC magnetic field, the electric conductivity σ is different between the completely quenched material and the unquenched material (raw material). Therefore, the values of the eddy current Je shown in Expression (2) are different between them. Then the magnetic flux density B also varies because the values of the eddy current Je are different.

$$Je = -j\sigma\omega\phi \quad (2)$$

In Expression (2), j denotes current density (A/m$^2$), a denotes electric conductivity (S/m), ω denotes angular frequency (ω=2πf), and φ denotes magnetic flux (Wb).

An output voltage V(V) can be expressed by the following Expression (3).

$$V = -N \cdot d\phi/dt \quad (3)$$

In Expression (3), N denotes the number of turns of the coil, and t denotes time (s). The magnetic flux density B of the workpiece 10 can be obtained from Expressions (1) and (2). The output voltage V can be obtained by using the magnetic flux density B obtained from Expressions (1) and (2); and Expression (3).

When the steel material is quenched, the permeability μ decreases. When the quenching depth in the workpiece 10 is relatively deep, the permeability μ of the entire workpiece 10 decreases. Although calculation with an equivalent magnetization circuit can be utilized if change of the permeability μ relative to change of the quenching depth is linear, changes are not linear. Therefore, the output voltage V for each quenching depth of the workpiece 10 is calculated by using a finite element method based on the permeability, the electric conductivity, and the initial magnetization curves of the completely quenched material and the unquenched material (raw material) and the output voltage V serves as an estimated voltage value predicted to be detected by the detection coil. In the quenching depth measurement method according to the present invention, the known electromagnetic characteristic information includes the estimated voltage value corresponding to the quenching depth of the workpiece obtained by the finite element method. Then specification of the quenching depth of the workpiece 10 is enabled through comparison between output voltage value of the workpiece 10 actually measured by the detection coil 5 and the quenching depth of the workpiece 10 included in the known electromagnetic characteristic information. Therefore, with the quenching depth measurement method according to the present invention, optimization in the shapes of the coil and the yoke as well as electric measurement conditions (such as frequency and current value) in advance is enabled by using the finite element method, and the man-hours for the determination of the conditions including the availability determination can be reduced.

To verify the analysis method according to the measurement method of the quenching depth according to the present invention, a testing material was used to measure an electromagnetic characteristics corresponding to the quenching depth, and the value was compared with an analytic value. A measurement method of the electromagnetic characteristics of the testing material will be described first. Electromagnetic characteristics of an unquenched material (raw material) and a completely quenched material of the same material were investigated in advance, and magnetization curves of the completely quenched material and the unquenched material (raw material) were obtained to evaluate the difference between the electromagnetic characteristics. A specific example of an acquisition method of known electromagnetic characteristic information will be described. First, two long testing materials made of the same material as the workpiece to be inspected were prepared and then one of the testing materials was not subjected to quenching to be the unquenched material (raw material), and the other testing material was subjected to quenching to be the completely quenched material. The electromagnetic characteristics of the testing materials were measured. For example, for the electric conductivity σ, each testing material was connected to a Kelvin bridge circuit, and the electric conductivity σ of the magnetized testing material was measured. For the permeability μ, electromagnets were arranged on both ends of the long testing material, and the magnetic flux density B and the applied magnetic field H of the testing material magnetized by the electromagnet were measured. The magnetic flux density B was measured by a coil wound around at a middle section of the testing material. The applied magnetic field H was measured by arranging a Hall element for applied magnetic field measurement near the coil for magnetic flux density measurement. The initial magnetization curves of the completely quenched material and the unquenched material (raw material) were obtained from the measurement result of the permeability μ. A plurality of steel materials with different quenching depths were prepared, and attenuation factors of output voltages and initial magnetization curves as electromagnetic characteristics were obtained by a method similar to the method described above.

Figure 2:
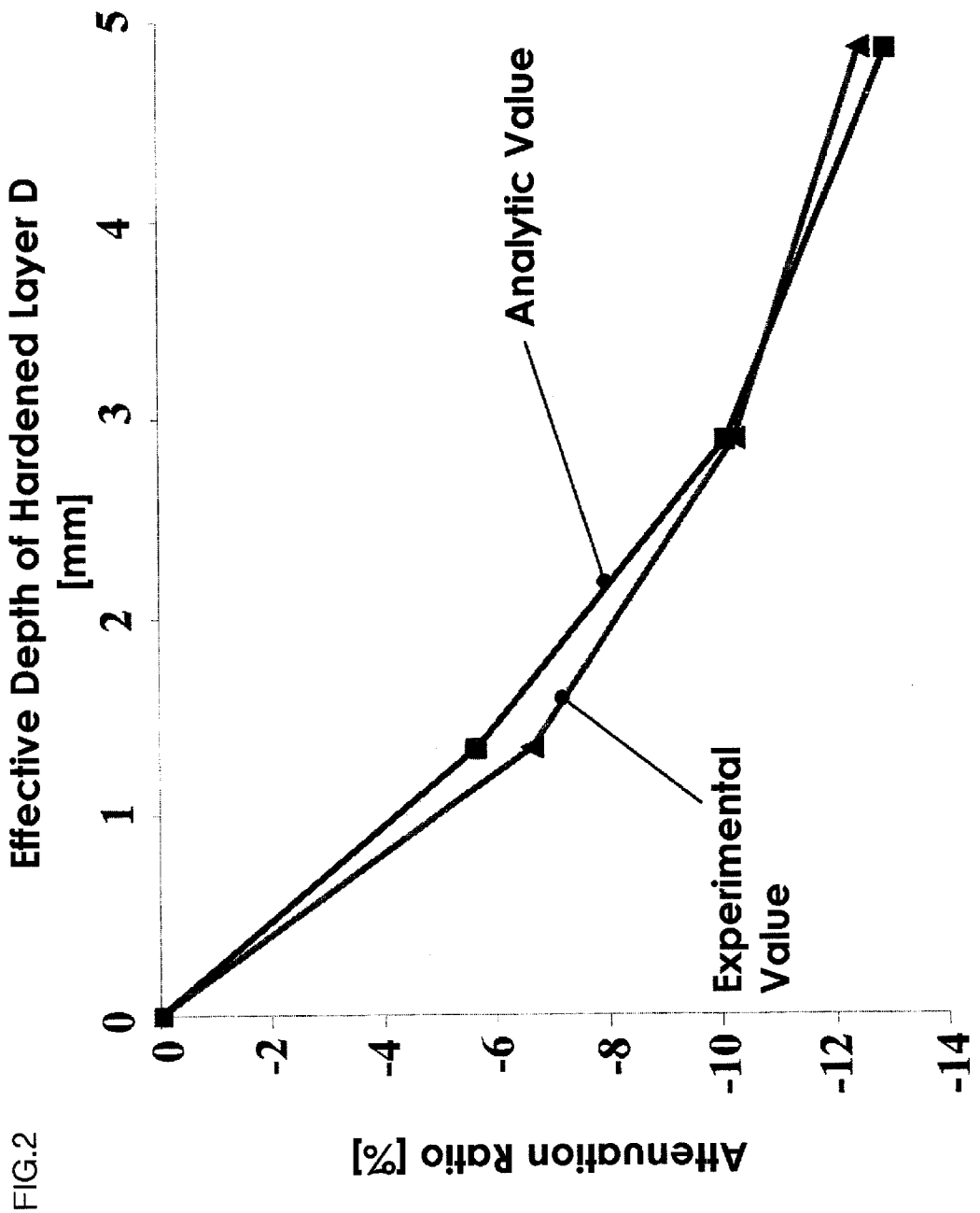
FIG. 2 is a graph for comparing an analytic value obtained by the quenching depth measurement method according to the present invention and an experimental value of a testing material obtained by actual measurement for verification.

A graph of FIG. 2 shows a relationship between the attenuation ratio and the quenching depth of the output voltage of the testing material obtained by the method. FIG. 2 also shows a relationship between the attenuation ratio of the output voltage and the quenching depth as electromagnetic characteristics in the analysis obtained by the finite element method adopted in the quenching depth measurement method according to the present invention. As shown in the graph in FIG. 2, the experimental values obtained by the actual measurement of the testing materials is approximately the same with the analytic values obtained by the quenching depth measurement method according to the present invention. Therefore, the analysis method used in the quenching depth measurement method according to the present invention can provide a highly reliable result. If the known electromagnetic characteristic information cannot be acquired as existing information in the case including when the workpiece as an object to be measured is made of a special material, the electromagnetic characteristic information can be acquired in advance by the method described above. The attenuation factor of the output voltage was calculated from the amount of change in the output voltage of the detection coil based on the unquenched material (raw material).

Next, a method of measuring the quenching depth of the workpiece 10 using the quenching depth measurement apparatus 1 according to the present invention will be described. The magnetizer 4 may include the yoke 2 and the excitation coil 3 wound around the yoke 2, as exemplified in FIG. 1. The magnetizer 4 is arranged near the surface of the workpiece 10. As exemplified in FIG. 1, the magnetizer 4 is arranged so that the opening section 22 of the yoke 2 is at a position separated by the specific gap L from the quenched surface of the workpiece 10. The gap L between the yoke 2 and the surface of the workpiece 10 may be a distance that allows the magnetizer 4 to sufficiently magnetize the workpiece 10 and the gap can be maintained. Certain current is supplied to the excitation coil 3 to generate a magnetic field, and the workpiece 10 is magnetized. The eddy current Je is generated on the surface of the workpiece 10 by the magnetization caused by the magnetizer 4, and induced electromotive force is generated by the eddy current Je. The induced electromotive force acts on the detection coil 5.

The quenching depth measurement apparatus according to the present invention includes means for detecting the induction magnetic field generated by the magnetization of the workpiece 10 caused by the magnetizer 4 by the detection coil 5 and measuring the output voltage of the detection coil 5. As exemplified in FIG. 1, the voltmeter 6 is connected to the detection coil 5 wound around the yoke 2 to measure the output voltage of the detection coil 5.

Figure 3:
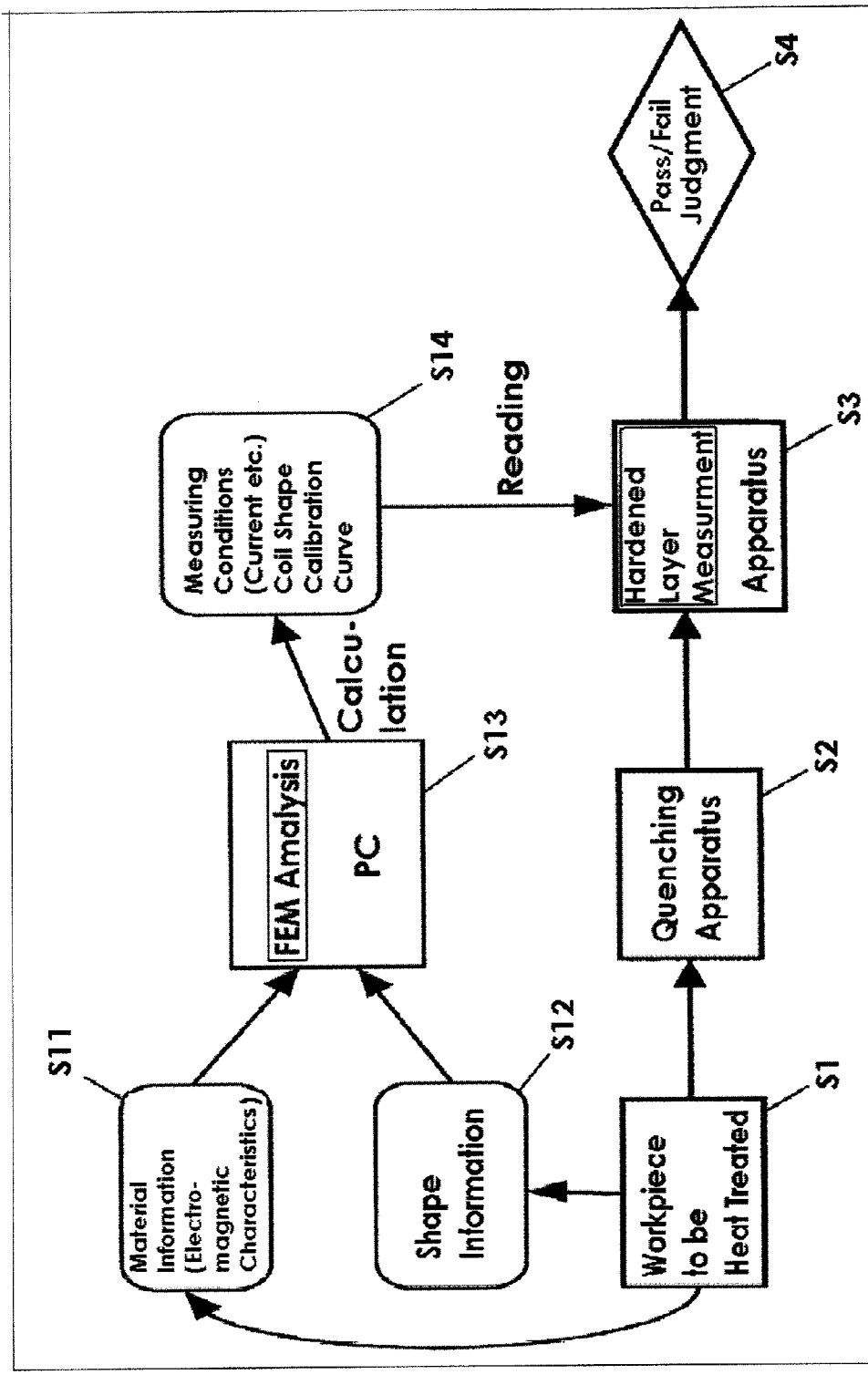
FIG. 3 is a flow chart demonstrating quenching depth measurement system according to an embodiment according to the present invention.

FIG. 3 is a flow chart demonstrating quenching depth measurement system in an embodiment according to the present invention. Hereinafter, quenching depth specifying system according to the present invention will be described with reference to FIG. 3. The quenching depth specifying system according to the present invention prepares a workpiece to be heat treated (step S1), quench the workpiece using a quenching apparatus (step S2), measure the depth of a quench hardened layer of the workpiece using a measurement apparatus (step S3), and judge pass/fail based on values obtained by the measurement (step S4). In the measurement, acquire material information (electromagnetic characteristic information) of the workpiece (step S11), and acquire shape information of the workpiece (step S12). Based on the acquired information, numerical analysis by the finite element method (FEM) is carried out using a computer (PC) (step S13). Data relating to the measurement conditions (such as current value), the coil shape, and the calibration curve is delivered from the computer (PC) (step S14), and the data is input to the main body of the measurement apparatus. More specifically, the quenching depth specifying mean specifies the thickness of the quench hardened layer 10a based on the measurement result of the output voltage in the detection coil 5 and the estimated output voltage value included in the known electromagnetic characteristic information. The quenching depth specifying means may be an arithmetic processing unit using a computer, and based on the method described above, the quenching depth specifying means specifies the quenching depth of the workpiece (thickness of the quench hardened layer) from the known electromagnetic characteristic information including the initial magnetization curves of both the unquenched material not subjected to quenching and the completely quenched material subjected to quenching and the output voltage value of the detection coil.

In the quenching depth measurement apparatus 1 according to the present invention, the magnetizer 4 may scan in an X axis direction of FIG. 1 (or Y axis direction of the workpiece 10 not shown), or the workpiece 10 may be moved while the position of the magnetizer 4 is fixed for magnetization of a desired position of the workpiece 10.

The position where the quenching depth is measured can be specified with a Z axis which line-symmetrically divides the yoke 2 and the X axis, the position of the surface of the workpiece 10 in the side view of the workpiece 10 as shown in FIG. 1. Although the hardened layer depth is usually measured at an instructed measurement position, visual check is difficult when the magnetic characteristics are used and it fails to make the measurement position accurate. However, in the quenching depth measurement method according to the present invention, the user can accurately figure out the measurement position based on the distribution of the current by using the finite element method. Therefore, when the thickness of the quench hardened layer 10a is specified at a plurality of portions, a graph of the quenching depth of the workpiece 10 can be accurately formed as shown in FIG. 4.

The magnetizer and the detection coil corresponding to the quenching depth measurement method and the quenching depth measurement apparatus according to the present invention are not limited to the construction shown in FIG. 1, and the construction at least include an excitation coil which enables magnetization of the workpiece 10. With the construction of the magnetizer 4 demonstrated in FIG. 1, as the arrangement of the magnetizer 4 near the surface of the quenched workpiece 10 makes measurement of the quenching depth possible, the quench hardening depth of the workpiece can be measured regardless of the size and the shape of the workpiece 10.

INDUSTRIAL APPLICABILITY

In the quenching depth measurement method according to the present invention, as calibration curve preparation is not required even though a non-destruction inspection, highly accurately quenching depth of the workpiece is acquired by using a simple apparatus, the method can contribute to an improvement in the quality of a component for which highly accurate identification of the quenching depth is desired.

Further, as the quenching depth measurement method according to the present invention can also be suitably used for a workpiece having shapes including a round-bar shape, a pipe shape or a flat shape, the method can be used regardless of the shape of the object to be measured, and may be applicable in a wide range of application. Furthermore, it is suitable to arrange the quenching depth measurement apparatus according to the present invention in a manufacturing line of the workpiece to perform full measurement of the quenching depth on all of workpieces.

In the technical concept of the quenching depth measurement method according to the present invention, the method may be applied to depth measurement of various hardened layers through filled electromagnetic data corresponding to the types of the material applied on principle of the quenching depth measurement method according to the present invention.

LIST OF SYMBOLS

1 . . . quenching depth measurement apparatus
3 . . . excitation coil
4 . . . magnetizer
5 . . . detection coil
10 . . . workpiece

The invention claimed is:

1. A quenching depth measurement method of measuring quenching depth in a workpiece, the method including:
   magnetizing the workpiece by arranging a magnetizer including an excitation coil near the workpiece;
   detecting an induction magnetic field generated by the magnetization by a detection coil to measure an output voltage of the detection coil; and
   determining a thickness of a quench hardened layer of the workpiece based on:
   known electromagnetic characteristic information on an unquenched material not subjected to quenching and made of a workpiece equivalent material;
   known electromagnetic characteristic information on a completely quenched material subjected to quenching and made of the workpiece equivalent material; and
   an output voltage value measured by the detection coil,
   wherein: the electromagnetic characteristic information includes an estimated output voltage value of the detection coil obtained by analysis based on a finite element method using initial magnetization curves and electric conductivities of the unquenched material made of a workplace equivalent material, and initial magnetization and electric conductivities of the completely quenched material made of a workpiece equivalent material.

2. A quenching depth measurement apparatus including:
   a magnetizer that magnetizes a workpiece;
   a detector configured to detect an induction magnetic field generated by the magnetization by a detection coil to measure an output voltage of the detection coil; and
   quenching depth calculator configured to calculate quenching depth of the workpiece from a measured output voltage value of the detection coil and known magnetic characteristic information relating to a workpiece equivalent material, wherein
   the quenching depth calculator is configured to determine the quenching depth of the workpiece from the known electromagnetic characteristic information including:
   an estimated output voltage value of the detection coil obtained by analysis based on a finite element method using initial magnetization curves and electric conductivities on an unquenched material not subjected to quenching,
   an estimated output voltage value of the detection coil obtained by analysis based on a finite element method using initial magnetization curves and electric conductivities on a completely quenched material subjected to quenching, and
   the output voltage value of the detection coil.

* * * * *